United States Patent
Ben-Shalom (10) Patent No.: US 9,000,149 B2
(45) Date of Patent: Apr. 7, 2015

(54) MIXTURE AND METHOD FOR REDUCING CHOLESTEROL USING HYDROPHOBIC MICROPARTICLES

(75) Inventor: Noach Ben-Shalom, Tel Aviv (IL)

(73) Assignees: Ben-Bar Technology 2006 Ltd., Ashrat (IL); Miloubar Central Feed Mill Corporation Ltd., Ashrat (IL)

( * ) Notice: Subject to any disclaimer, the term of this patent is extended or adjusted under 35 U.S.C. 154(b) by 471 days.

(21) Appl. No.: 12/518,115

(22) PCT Filed: Dec. 6, 2007

(86) PCT No.: PCT/IL2007/001513
§ 371 (c)(1), (2), (4) Date: Jun. 8, 2009

(87) PCT Pub. No.: WO2008/068763
PCT Pub. Date: Jun. 12, 2008

(65) Prior Publication Data
US 2010/0048508 A1    Feb. 25, 2010

Related U.S. Application Data

(60) Provisional application No. 60/873,159, filed on Dec. 7, 2006.

(51) Int. Cl.
*A61K 31/722* (2006.01)
*A61P 3/06* (2006.01)
*A61K 9/16* (2006.01)
*A23K 1/16* (2006.01)
*A23K 1/18* (2006.01)

(52) U.S. Cl.
CPC ............. *A61K 9/1617* (2013.01); *A23K 1/164* (2013.01); *A23K 1/1643* (2013.01); *A23K 1/1826* (2013.01); *A61K 9/1652* (2013.01); *A61K 31/722* (2013.01)

(58) Field of Classification Search
USPC ................................. 536/85; 524/42; 424/494
See application file for complete search history.

(56) References Cited

U.S. PATENT DOCUMENTS 3,620,776 A * 11/1971 Mishkin et al. .............. 34/288
5,518,736 A * 5/1996 Magdassi et al. ............ 424/451

FOREIGN PATENT DOCUMENTS

WO    WO 2004/080438 A1 * 9/2004 ............. A61K 9/127

OTHER PUBLICATIONS

Tong et al, Carbohydrate Polymers, 2005, 60, 229-33.*
Murata et al, Biol. Pharm. Bull. 2004, 27(3), 440-42.*

* cited by examiner

*Primary Examiner* — Ganapathy Krishnan
(74) *Attorney, Agent, or Firm* — Mark M Friedman (57) ABSTRACT

The present invention relates to mixtures including hydrophobic microparticles comprising a positively charged polymer (e.g. a polysaccharide such as chitosan) non-covalently bound to an anionic or non-ionic surfactant such as lecithin. The mixtures are useful for reducing cholesterol of an animal, for example a bird such as a chicken or any type of mammal. Methods of manufacture and use of the mixtures are also disclosed herein.

13 Claims, 5 Drawing Sheets

```
┌─────────────────────────────┐              ┌──────────────────┐
│ S201 Dissolve Chitosan (1.5%)│              │ S203 Dissolve    │
│    in 0.75% HCl and          │              │ Lecithin 7.5% in │
│  mix for one or more hours to│              │ water to form a  │
│    form a first solution     │              │ second solution  │
└──────────────┬───────────────┘              └────────┬─────────┘
               │                                       │
               └───────────────┬───────────────────────┘
                               ▼
          ┌──────────────────────────────────────────┐
          │ S205 Mix first and second solution       │
          │ in a given ratio (for example, to establish a│
          │ chitosan:lechitin Ration of between 0.2:1│
          │        and 5:1) at pH of 3.5             │
          └──────────────────┬───────────────────────┘
                             ▼
          ┌──────────────────────────────────────────┐
          │  S207 – Spray Drying to a powder form    │
          └──────────────────────────────────────────┘
```

MIXTURE AND METHOD FOR REDUCING CHOLESTEROL USING HYDROPHOBIC MICROPARTICLES

FIELD OF THE INVENTION

The present invention relates to mixtures including hydrophobic microparticles comprising a positively charged polymer (e.g. a polysaccharide such as chitosan) chemically bound to an anionic or non-ionic surfactant such as lecithin. The mixtures are useful for reducing cholesterol of an animal, for example a bird such as a chicken or any type of mammal. Methods of manufacture and use of the mixtures are also disclosed herein.

BACKGROUND OF THE INVENTION

Cholesterol is a sterol lipid found in the bloodstream and in the cell membranes of all body tissues.
The structure of cholesterol is as follows:

Cholesterol is composed of three regions: a hydrocarbon tail; a ring structure region with 4 hydrocarbon rings; and a hydroxyl group. The hydroxyl group is polar, which makes it soluble in water. The ring region and tail region are non-polar, so are soluble in organic solvents, but insoluble in water.

Medical practitioners and health advisors recommend reducing intake of cholesterol since elevated LDL blood cholesterol level (hypercholesterolemia) may lead to slow build up of cholesterol deposits in the walls of the arteries feeding the heart and brain, forming a plaque which can clog these arteries, a condition known as artherosclerosis. A clot (thrombus) that forms near this plaque can block the blood flow to part of the heart muscle and cause a heart attack. If such a clot blocks the blood flow to part of the brain, a stroke results. A high level of LDL cholesterol (160 mg/dL and above) reflects an increased risk of heart disease.

Chicken eggs represent a very high source of cholesterol (typically approximately 280 mgs per large egg) many medical practitioners and health consultants recommend eliminating eggs from the diet of those having high cholesterol blood serum concentrations. Consequently, for persons having cholesterol levels that are considered too high, conventional chicken eggs are almost eliminated as a source of food. This is somewhat unfortunate since eggs represent a substantial source of protein, vitamins, minerals and other nutrients in a form which is considered to be high in quality, nutrition and density while being relatively low in cost.

Because of the nutritional value of eggs, research poultry scientists have been experimenting to attempt to have chickens lay lower cholesterol eggs. One system, which has been tried, is the addition of foreign deleterious chemicals to the daily rations of egg laying hens. Also, hens have been injected with synthetic hormones to produce the desired reduction in cholesterol level. This present approach was prompted by the knowledge that cholesterol levels in the blood of humans can be controlled medically with hormones, calcium and magnesium ions, high doses of niacin and other vitamins and the use of throid active substances. As would be expected, such treatments exhibit in a great many instances deleterious and adverse side effects.

It has also been found that drugs are not cost effective as a feed supplement in lowering total blood cholesterol and improving the HDL/LDL ratio in barn animals (Luhman et al., Poultry Science 69: 852-855 (1990); Mori, et al., J.).

One method of reducing total cholesterol and improving the HDL-LDL ratio is by feeding animals especially chickens compounds that sequester bile salts which prevent their reabsorption by the lower small intestine causing their consequent excretion. Increased fecal bile acid excretion induces the liver to produce more bile acids, utilizing cholesterol as a substrate in its production. The resulting acceleration in LDL catabolism has the effect of reducing cholesterol content in the blood and improving the HDL-LDL ratio.

Chitosan is the only naturally occurring, positively charged polysaccharide, and is generally produced by deacetylation of chitin, a naturally occurring biopolymer, found in the cytoskeleton and hard shells of marine organisms such as crustacea, shrimps, crabs, fingi, etc.

Chitosan

It has been found that chitosan is able to absorb blood cholesterol in small animals (particularly mice and rats), as well as bile lipids, thereby lowering the blood levels of these molecules [J. Nutr. 2000; 130: 2753-2759]. A number of studies have shown that chitosan has the unique ability to lower levels of "bad" LDL cholesterol, while boosting "good" HDL cholesterol levels, thereby improving the HDL/LDL ratio.

Chitosan is biocompatible, non-toxic, and non-immunogenic, allowing its use in the medical, pharmaceutical, and cosmetic fields.

The soluble form of chitosan contains positively charged amino groups that are able to form ionic bonds with anionic compounds, including proteins and fatty acids. Additionally, chitosan may form hydrophobic bonds.

In order to use chitosan in aqueous solution, dissolution of the crystalline structure must take place. In hydrated crystalline chitosan, water molecules form columns between chitosan sheets and contribute to stabilizing the structure by making water-bridges between polymer chains. The hydrogen bonds are broken during the dissolution process of the chitosan using weak organic acids like acetic acid.

The mechanism of dissolution of polyelectrolyte powders is believed to involve the formation of a spherical grain structure. In pure water, this includes the rapid formation of a gel layer around the particle, followed by the slow release of polymer chains into the solvent. The slow process of polymeric chains leaving an aggregate was explained as being due to the effect of an attractive potential forming between the charged individual polymer and the electroneutral aggregate.

It is known that equilibration times for the dissolution of polyelectrolytes are often in the order of hours and even many days (Michel, R C et al. *Biopolymers* 53:19-39, 2000; Reed W F et al. *Ber Bunzen Phys Chem* 100: 685-695, 1996). The duration time of stirring of the chitosan solution is reported to be 12-24 h at room temperature Fredheim G E et al *Biomacromolecules* 4:232-239, 2003.

It has been found that chitosan is able to absorb blood cholesterol in small animals (particularly mice and rats), as well as bile lipids, thereby lowering the blood levels of these molecules [*J. Nutr.* 2000; 130: 2753-2759] A number of studies have shown that chitosan has the unique ability to lower levels of "bad" LDL cholesterol, while boosting "good" HDL cholesterol levels.

Cholesterol is a precursor of bile acids, which are steroid acids found mainly in the bile of mammals, having both a hydrophilic and a hydrophobic face. It has been suggested that chitosan reduces blood cholesterol by absorption of bile acids, causing increased use of cholesterol in further synthesis of bile acids, thereby removing cholesterol from the blood.

A food fiber supplement comprising chitosan and glucomannan has been shown to lower blood cholesterol in rats [*J. Nutr.* 2000; 130: 2753-2759] and in humans [*J. Am. College Nutrition* 2002; 21(5): 428-433]. However, large amounts of the fiber supplement were required in order to produce the cholesterol-lowering effect in humans, requiring the ingestion of fifteen capsules per day, providing 1.2 g/day each of chitosan and glucomannan. The total serum cholesterol in the human study was lowered by only about 7%, and the LDL cholesterol by 10%.

U.S. Pat. Nos. 7,067,146 and 6,814,975; U.S. patent Application No. 20050079204; and European Patent No. 1233682 to Eritocap teach use of chitosan together with eritadenine in the preparation of a foodstuff for reduction of cholesterol.

U.S. Pat. No. 6,323,189 and European Patent No. 1100344 teach a stable chitosan-containing liquid suspension for weight treatment.

U.S. patent Application No. 20050175763 teaches a phospholipd-containing stable matrix consisting of a supporting material in the form of a carbohydrate, such as chitosan. U.S. patent Application No. 20050100619 teaches a cholesterol-lowering supplement which may include chitosan and a phospholipid, together with a further composition capable of inhibiting cholesterol biosynthesis and a composition capable of increasing cholesterol metabolism.

Chitosan is unable to reduce cholesterol in the stomach, since it cannot absorb non-emulsified fats in the absence of bile salts, which are secreted only in the small intestine. Furthermore, chitosan dissolves and becomes positively charged in the acid conditions of the stomach, due to its functional amino groups. The highly charged polymer can react strongly with negatively-charged materials, such as phospholipids, which are present in the stomach, and become partially saturated. As a result, the amount of ingested chitosan having positively-charged groups available for interaction with the negatively charged bile acids after passing through the stomach is decreased.

There is thus a widely recognized need for, and it would be highly advantageous to have an improved mixture comprising chitosan which provides delivery of an increased proportion of unsaturated chitosan to the small intestine, for reducing blood cholesterol in animals, such as birds or mammals.

SUMMARY OF THE INVENTION

It is now disclosed for the first time a mixture useful for cholesterol treatment, the mixture comprising a plurality of composite particles, each composite particle including chitosan chemically bound to an anionic or non-ionic surfactant.

According to some embodiments, the anionic surfactant is selected from the group consisting of phospholipids; bile salts; sodium lauryl ether sulfate; citric acid esters of monoglycerides; sodium, calcium or acid stearoyl lactylate; stearyl citrate; fatty acids or salts thereof; diacetyl tartaric acid esters of monoglycerides; or combinations thereof.

According to some embodiments, the phospholipid comprises lecithin.

According to some embodiments, wherein the non-ionic surfactant is a fatty alcohol.

It is now disclosed for the first time a mixture useful for cholesterol treatment, the mixture comprising a plurality of hydrophobic composite particles, each composite particle including a cationic polymer chemically bound to an anionic or non-ionic surfactant.

According to some embodiments, the cationic polymer comprises chitosan.

According to some embodiments, the cationic polymer comprises a polyamine.

According to some embodiments, the polyamine comprises polylysine or polyacrylamide.

According to some embodiments, the surfactant is selected from the group consisting of phospholipids; bile salts; sodium lauryl ether sulfate; citric acid esters of monoglycerides; sodium, calcium or acid stearoyl lactylate; stearyl citrate; fatty acids or salts thereof; diacetyl tartaric acid esters of monoglycerides; or combinations thereof.

According to some embodiments, the phospholipid includes lecithin.

It is now disclosed for the first time a mixture useful for cholesterol treatment, the mixture comprising a plurality of chitosan-lecithin composite particles, each composite particle including chitosan chemically bound to lecithin.

According to some embodiments, the mixture is a dry mixture whose water content is at most 10% w/w.

According to some embodiments, the mixture is a dry mixture the water content is at most 20% w/w.

According to some embodiments, the mixture is a dry mixture the water content is at most 30% w/w.

This specific water content of the dry mixture may depend on the specific application.

According to some embodiments, the dry mixture is provided as a flowing powder.

According to some embodiments, the dry mixture is provided as a packed powder.

According to some embodiments, the dry mixture is provided as a mixture of granular particles.

According to some embodiments, the composite particles of the mixture are capable, upon mixing 2.5 grams of the composite particles of the mixture with 1 liter of a sodium cholate solution having a sodium cholate concentration of 0.5% w/w, of removing at least 10% of free sodium cholate from the sodium cholate solution within 30 minutes.

According to some embodiments, the composite particles of the mixture are capable, upon mixing 2.5 grams of the composite particles of the mixture with 1 liter of a sodium cholate solution having a sodium cholate concentration of 0.5% w/w, of removing at least 20% of free sodium cholate from the sodium cholate solution within 30 minutes.

According to some embodiments, the composite particles of the mixture are capable, upon mixing 2.5 grams of the composite particles of the mixture with 1 liter of a sodium cholate solution having a sodium cholate concentration of 0.5% w/w, of removing at least 30% of free sodium cholate from the sodium cholate solution within 30 minutes.

According to some embodiments, the composite particles of the mixture are capable, upon mixing 2.5 grams of the composite particles of the mixture with 1 liter of a sodium cholate solution having a sodium cholate concentration of 0.5% w/w, of removing at least 40% of free sodium cholate from the sodium cholate solution within 30 minutes.

According to some embodiments, chitosan of the composite particles has a molecular weight in the range of from $0.5 \times 10^5$ to $3 \times 10^6$ daltons.

According to some embodiments, at least 10%, by mass, of the composite particles of the mixture have a size between 0.3 microns and 2 microns.

According to some embodiments, at least 30%, by mass, of the composite particles of the mixture have a size between 0.3 microns and 2 microns.

According to some embodiments, at least 50%, by mass, of the composite particles of the mixture have a size between 0.3 microns and 2 microns.

According to some embodiments, at least 70%, by mass, of the composite particles of the mixture have a size between 0.3 microns and 2 microns.

According to some embodiments, at least 90%, by mass, of the composite particles of the mixture have a size between 0.3 microns and 2 microns.

According to some embodiments, excluding particles whose size is less than 0.3 microns, at least 10% by number of the composite particles of the mixture have a size that is less than 2 microns.

According to some embodiments, excluding particles whose size is less than 0.3 microns, at least 50% by number of the composite particles of the mixture have a size that is less than 2 microns.

According to some embodiments, excluding particles whose size is less than 0.3 microns, at least 90% by number of the composite particles of the mixture have a size that is less than 2 microns.

According to some embodiments, i) the composite particles of the mixture are capable, upon mixing 2.5 grams of the composite particles of the mixture with 1 liter of a sodium cholate solution having a sodium cholate concentration of 0.5% w/w, of removing at least 15% of free sodium cholate from the sodium cholate solution within 30 minutes; and ii) at least 30%, by mass, of the composite particles of the mixture have a size between 0.3 microns and 2 microns.

According to some embodiments, i) the composite particles of the mixture are capable, upon mixing 2.5 grams of the composite particles of the mixture with 1 liter of a sodium cholate solution having a sodium cholate concentration of 0.5% w/w, of removing at least 35% of free sodium cholate from the sodium cholate solution within 30 minutes; and ii) at least 30%, by mass, of the composite particles of the mixture have a size between 0.3 microns and 2 microns.

According to some embodiments, the plurality of composite particles include composite particles having a lechitin-chitosan mass ratio of between 0.2:1 and 5:1.

According to some embodiments, the plurality of composite particles include composite particles having a lechitin-chitosan mass ratio of between 3:1 and 4:1.

According to some embodiments, the chitosan and the lecithin of the composite particles are chemically bound by at least one of ionic and hydrophobic interactions.

According to some embodiments, the chitosan and the lecithin of the composite particles are not covalently bound with each other.

According to some embodiments, chitosan of the composite particles has a degree of acetylation of between 50% and 95%.

According to some embodiments, the mixture further includes: c) at least one animal feed product selected from the group consisting of a meat (for example, beef or fowl meet—this may be useful in dogfood or catfood), a grain (for example, wheat or oats—this may be useful in chicken feed or horse food), a plant seed, a corn (this may be useful, for example, in chicken feed), and a legume (for example, soybeans or a soybean product—this may be useful, for example, in chicken feed).

According to some embodiments, a sum of a protein-derived and a carbohydrate-derived nutritional value of the mixture is at least 2 calories per gram of the mixture.

According to some embodiments, a weight ratio within said mixture between a weight of said animal feed product in said mixture and a weight of said composite particles is at least 100:1, and wherein said composite particles are mixed substantially homogenously with said animal feed product.

It is now disclosed for the first time a method of creating a feed mixture, the method comprising: a) mixing any presently disclosed mixture with at least one animal feed product selected from the group consisting of a meat, a grain a plant seed, a corn, and a legume.

The mixture may be any mass ratio. In one example, at least 0.5%, or at least 0.1%, or at least 0.2%, or least 0.3% of the total weight of the mixture is composite particles.

The mixture may be any mass ratio. In one example, at most 1%, or at most 0.5%, or at most 0.3%, of the total weight of the mixture is composite particles.

It is now disclosed for the first time a method of feeding an animal comprising feeding any presently disclosed mixture to an animal.

According to some embodiments, the animal is selected from the group consisting of a bird (for example, a chicken), a pig, a cow, a horse, a cat, a lamb and a dog.

It is now disclosed for the first time a method of composite particle production, the method comprising: a) providing a plurality of chitosan particles; b) mixing the plurality of chitosan particles into an acid for at least 1 hour to obtain a first solution; c) preparing a second solution comprising an anionic or non-ionic surfactant; d) mixing the first and second solutions under acidic conditions to form chitosan-surfactant composite particles including chitosan chemically bound to the surfactant; and e) forming a powder from the chitosan-surfactant composite particles.

It is now disclosed for the first time a method of composite particle production, the method comprising: a) providing a plurality of chitosan particles; b) mixing the plurality of chitosan particles into an acid for at least 1 hour to obtain a first solution; c) preparing a second solution comprising lecithin; d) mixing the first and second solutions under acidic conditions to form chitosan-lecithin composite particles including chitosan chemically bound to lecithin; ande)

effecting a drying to form a powder from the chitosan-surfactant composite particles.

According to some embodiments, i) the mixed plurality of chitosan particles are, by weight, primarily low molecular weight chitosan particles having a weight between $0.3 \times 10^5$ and $1.5 \times 10^5$ daltons and ii) the mixing of step (b) is carried out for at least one hour.

According to some embodiments, i) the mixed plurality of chitosan particles are, by weight, primarily medium molecular weight chitosan particles having a weight between $1.5 \times 10^5$ and $5 \times 10^5$ daltons; and ii) the mixing of step (b) is carried out for at least two hours.

According to some embodiments, i) the mixed plurality of chitosan particles are, by weight, primarily high molecular weight chitosan particles having a weight between $0.5 \times 10^6$ and $3 \times 10^6$ daltons; and ii) the mixing of step (b) is carried out for at least three hours.

According to some embodiments, the mixing of step (b) is carried out for at least 20 hours.

According to some embodiments, the powder forming of step (d) includes at least one drying operation selected from the group consisting of: i) spray-drying; and ii) lyophilization According to some embodiments, the mixing of step (d) is carried out so that the first and second solutions are mixed together, before the stage of powder-forming, for a time period that is at least 2 minutes and at most 30 minutes, and an average temperature during the time period is less than 40 degrees Celsius.

According to some embodiments, the time period is at most 20 minutes.

According to some embodiments, the average temperature is less than 30 degrees Celsius.

According to some embodiments, the mixing of step (d) is carried out so that the first and second solutions are mixed together, before the stage of powder-forming, for a time period that is at least 2 minutes and at most 10 minutes, and an average temperature during the time period is less than 50 degrees Celsius.

According to some embodiments, the average temperature is less than 45 degrees Celsius.

According to some embodiments, the mixing of step (d) is carried out at a temperature and mixing time duration so that at least 10% by mass of the formed composite particles have a size that is between 0.3 and 2 microns.

According to some embodiments, the mixing of step (d) is carried out at a temperature and mixing time duration so that at least 50% by mass of the formed composite particles have a size that is between 0.3 and 2 microns.

According to some embodiments, the mixing of step (d) is carried out at a temperature and mixing time duration so that at least 70% by mass of the formed composite particles have a size that is between 0.3 and 2 microns.

According to some embodiments, in the acid is an organic acid selected from the group consisting of lactic acid and glutamic acid According to some embodiments, the second solution is prepared in an aqueous solution.

According to some embodiments, a concentration of the chitosan in the mixture of the first solution is between 0.25% w/w to 1% w/w.

According to some embodiments, a concentration of the chitosan in the mixture of the first solutions is between 0.1% w/w 2% w/w.

According to some embodiments, a concentration of the lecithin in the mixture of the second solution is between 1.25% w/w to 5.0% w/w.

According to some embodiments, a concentration of the lecithin in the mixture of the second solutions is between 0.1% w/w to 7.5% w/w.

According to some embodiments, a pH of the acid of step (b) is adjusted to a value of 3.5

According to some embodiments, the method further comprises the step of adjusting a pH of the mixture of the first and second solutions to a value of 7.

According to some embodiments, the method further comprises the step of allowing the mixture of the first and second solutions to stand for 30 minutes, then filtering to remove particles.

According to some embodiments, the method further comprises the step of resuspending the removed particles in an acid medium.

It is now disclosed for the first time a method for increasing cholesterol reduction in animals other than humans by chitosan, the method comprising increasing the hydrophobicity of the chitosan.

According to some embodiments, the hydrophobicity is increased by reacting chitosan with an anionic or non-ionic surfactant.

It is now disclosed for the first time a use of any mixture or method of any disclosed herein for reduction of body fat of an animal other than a human being.

It is now disclosed for the first time a use of any mixture or method disclosed herein in the treatment of obesity of an animal other than a human being.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the figures.

DESCRIPTION OF THE PREFERRED EMBODIMENTS

The present invention provides a mixture useful for cholesterol treatment comprising a plurality of composite particles where each composite particle includes a cationic polymer, for example chitosan, chemically bound to an anionic or non-ionic surfactant, for example lecithin.

The chitosan and the surfactant in the composite particles are chemically bound to form composite particles, due to ionic interactions between the cationic polymer, and the anionic surfactant, as well as hydrophobic interactions between the hydrodphobic regions of the polymer and the lipid fraction of the lecithin during drying of the particles. The interaction between the cationic polymer and non-ionic surfactants involves non-ionic interactions.

In exemplary embodiments, the cationic and the anionic polymer are not covalently bounded to each other.

In one preferred embodiment, the composite particles comprise chitosan chemically bound to lecithin.

The presently disclosed composite particles may be useful for cholesterol reduction.

In particular, when administered to chickens (for example, mixed in with chicken feed) the presently disclosed composite particles may be useful for reduction of cholesterol in a chicken, and reduction of cholesterol in eggs provided by the chickens. As a result, the chicken eggs can remain a nutritious and relatively cheap food for humans without having deleterious effects on hepatic and aortic cholesterol levels.

Theoretical Discussion

Not wishing to be bound by theory, it is noted that in exemplary embodiments, the composite particles simultaneously provide three properties. In these embodiments, the composite particles (i) are hydrophobic particles capable of binding bile acids in the intestine (ii) are capable, at an intestinal pH, of forming a partially stable suspension—for example, due to particle size and (iii) are soluble in the stomach.

As noted earlier, bile cholesterol is a precursor of bile acid. By introducing a hydrophobic particle into the intestine that is capable of being suspended for some period of time in the intestine, it is thus possible to flush bile acid out of the intestine. Over time, it is hypothesized that this is useful for reducing cholesterol in an animal which ingests a composite particles. Thus, not wishing to be bound by theory, it is noted that the first of the three aforementioned properties is useful for binding with bile acid in the intestine.

As for the second of the aforementioned three properties, it is noted that the composite particles are designed such that upon entry into the human intestine, the particles remain for a short time as a stable particle suspension in intestinal medium, while interaction with bile salts takes place. The composite particles then precipitate as an agglomerate with the bile salts. Bile salts are thus trapped inside the polymer through hydrophobic interactions, and prevented from undergoing hydrolysis during passage through the intestine.

The time for which the particles remain in suspension should be sufficient to enable interaction with bile salts to occur. Particles which are incapable of forming an at least partially stable solution will undergo rapid flocculation in intestinal fluid, such that binding and entrapment of bile salts is not able to occur.

This property may be attributable, for example, to the particle size. Thus, in exemplary embodiments, the particles are microparticles having a size of between 0.3 and 3 microns.

As for the third of the aforementioned three properties, it is noted that in some embodiments, the composite particles should be soluble in the stomach and delivered to the human small intestine in an effective form for binding bile acids. According to these embodiments, the composite particles are stable and substantially unreactive in the environment of the human stomach, such that they are delivered to the intestine in soluble, unsaturated form.

A Discussion of Hydrophobicity

As stated previously, Chitosan is a positively charged polysaccharide polymer that is indigestible and therefore excreted.

Lecithin has been characterized as an emulsifier/detergent, which binds bile salt preventing their absorption in the small intestine (Lipids. 1976 December; 11(12):830-2). Lecithin is a mixture of low cost, natural, glycolipids, triglycerides, and negatively charged phospholipids. At least one embodiment of the present invention uses lecithin rich in phospholipids, however normal lecithin with much higher neutral lipids or other lecithin with different lipids composition can be used.

Not wishing to be bound by any particular theory, it was hypothesized by the present inventor, that non-ionic surfactants may chemically bind chitosan molecules via interaction with the hydrophobic tail region, resulting in the formation of an uncharged chitosan-surfactant composite particle that is water-insoluble at the pH of the intestine. It was thus considered that increasing the hydrophobicity of chitosan would increase its binding to bile acids in certain animals, for example, in chickens.

It was considered by the present inventor that absorption of bile acids by chitosan in small animals occurs as a result of non-specific ionic interactions between the positively-charged chitosan polymer (which competes with many other positively-charged blood proteins) and the negatively-charged bile acids, while binding of chitosan to the hydrophobic face of bile acids would be much more specific.

It was hypothesized by the present inventor that non-ionic surfactants may absorb chitosan molecules via interactions with the hydrophobic tail region, resulting in the formation of an uncharged chitosan molecule that is water-insoluble at the pH of the intestine. It was thus considered that increasing the hydrophobicity of chitosan would increase its binding to bile acids in animals, such as chicken.

It is thus noted that the present invention provides a method of elevating a hydrophobicity of chitosan particles by providing "composite" particles of chitosan chemically bound with a surfactant such as lecithin.

Not wishing to be bound by theory, it is noted that the presently disclosed composite particles having a strong hydrophobic region, which are soluble in the acid conditions of the stomach, may enter the small intestine in solution, wherein the microparticles bind bile salts and then precipitate.

It has been shown by Magdassi et al. of the Hebrew University, Jerusalem, Israel (see, for example, G. Nizri and S. Magdassi: Solubilization of hydrophobic molecules in nanoparticles formed by polymer-surfactant interactions, *J. Colloid Interface Sci.* 291, 169-174 (2005)) that when a polycationic polymer is mixed with an anionic surfactant, electrostatic interactions lead to precipitation of nanoparticles. Such particles are capable of solubilizing hydrophobic molecules due to the formation of hydrophobic pockets in the polycationic polymer. Magdassi did not teach or suggest the use of hydrophobic microparticles comprising chitosan for reducing cholesterol in humans. Furthermore, Magdassi only studied nanoparticles and not microparticles.

Magdassi teaches, in U.S. Pat. No. 5,753,264, preparation of a positively charged chitosan-containing aqueous emulsion of a oil, wherein an aqueous chitosan solution is added to an oil-in-water emulsion comprising an anionic emulsifier, to produce an insoluble surfactant-chitosan complex. The emulsifier may comprise lecithin. The purpose of the patent to Magdassi is stabilization of the oil. No particles of chitosan and lecithin are formed, but rather a stable emulsion of lecithin is first formed, to which chitosan is then added. The ratio of chitosan to lecithin used by Magdassi is 0.5:033. The process was carried out at pH 6. If the pH of the emulsion described by Magdassi were to be increased to above 7, at the chitosan:lecithin ratio used, precipitation of chitosan would immediately result, before interaction with bile acids could occur.

It has surprisingly been found by the present inventor that a mixture comprising a positively charged polymer such as chitosan and an anionic or non-ionic surfactant, such as lecithin, provides composite hydrophobic microparticles, wherein chitosan is prevented from undergoing ionic interactions with positively charged molecules in the stomach, such that the chitosan is delivered to the intestine in a state which is readily available for binding bile acids.

The mixtures provided by embodiments of the present invention preferably comprise particles that are able to interact with bile salts to form a complex with passes through the small intestine in the form of an at least partially stable, insoluble suspension, in order to prevent digestion and disintegration by free bile salts which are able to break down the particles and interact with the lecithin.

A mixture comprising such composite microparticles would therefore be highly useful in binding bile acids and thereby reducing LDL cholesterol levels in various animals.

The composite particles of exemplary embodiments are soluble in the acidic conditions of the stomach and form suspended particles in the higher pH environment of the human small intestine. Such particles are able to interact with bile salts through hydrophobic interactions with the hydrophobic part of the bile salts, resulting in precipitation to form an insoluble agglomerate, within which the bile salts are trapped. In order to achieve this effect, the composite particles should be sufficiently hydrophobic to provide strong hydrophobic interactions with the hydrophobic region of bile salts.

In some embodiments, the particles are designed such that upon entry into the human intestine, the particles remain for a short time as a stable particle suspension in intestinal medium, while interaction with bile salts takes place. The particles then precipitate as an agglomerate with the bile salts. Bile salts are thus trapped inside the polymer through hydrophobic interactions, and prevented from undergoing hydrolysis during passage through the intestine.

The time for which the particles remain in suspension must be sufficient to enable interaction with bile salts to occur. Particles which are incapable of forming an at least partially stable solution will undergo rapid flocculation in intestinal fluid, such that binding and entrapment of bile salts is not able to occur.

Thus, in some embodiments, the particles of the present invention are capable of providing an at least partially stable suspension in intestinal medium and are sufficiently hydrophobic to react strongly with the hydrophobic region of bile salts, and form a precipitate with bile salts In experiments conducted by the present inventor, it was found that absorption of bile salts by the lecithin:chitosan particles of the present invention is affected by hydrophobic degree and particle size. The hydrophobic degree may be controlled by the lecithin concentration in the particles and/or the type of lecithin used.

A Discussion of Particle Size and Particle Size Distribution

The present inventor is now disclosing that particles in the size range of 0.3 microns to 2 microns in some embodiments, and particles in the size range of 0.3 to 1.5 microns in some embodiments, which are capable, upon entering the intestinal pH to form an at least partially stable suspension and after, bind bile salts.

It is recognized that in any given mixture, the particle size of the composite particles, is not going to be identical for every particle in the mixture. Instead, any given mixture will have a particle size distribution.

In exemplary embodiments, a certain minimum percentage of the particles have a size in a given size range, for example, between 0.3 microns and 2 microns, or between 0.3 microns and 1.5 microns. Not wishing to be bound by theory, it is noted that this size range may be useful for providing particles which, when introduced into the intestine, are capable of forming a partially stable suspension. Thus, larger particles may precipitate before binding bile acid, and may not have be effective for flushing the bile acid out of the intestine. Smaller particles could form a completely stable suspension, and may be less useful for "eventually sinking after binding with bile acid" and flushing the bile acid out of the intestine. Furthermore, the smaller particles may be more susceptible to enzymatic digestion.

Thus, in some embodiments, the particles in the aforementioned size range are "active material" for removing bile acid.

Therefore, in some embodiments, a certain minimum percentage of complex particles, either by weight or by number, have a size in the target size range.

Figure 1:
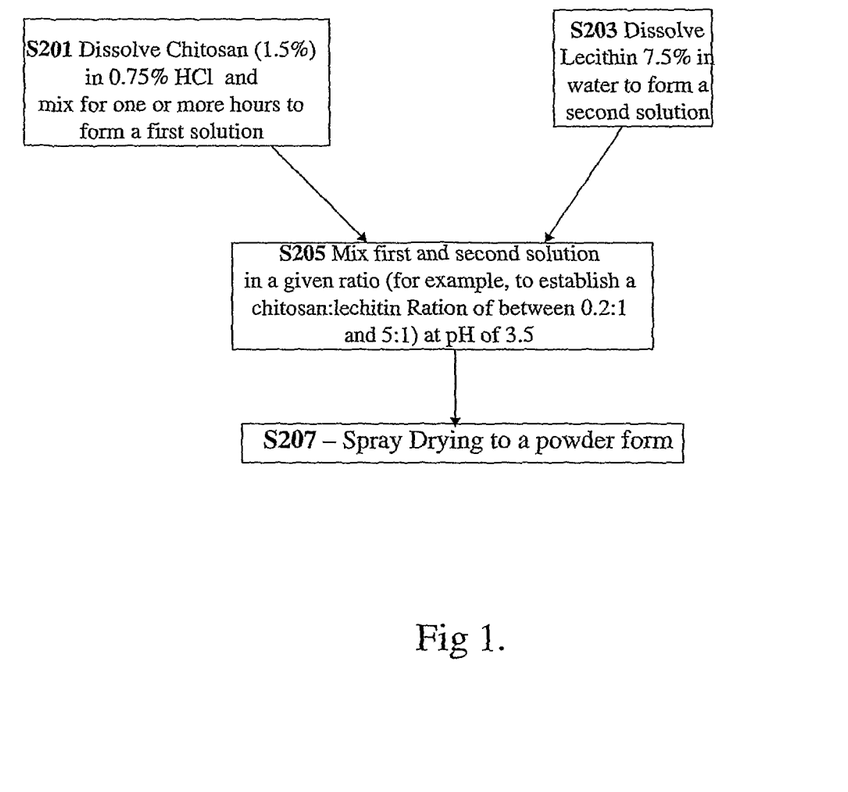
FIGS. 1-2 are flow charts of exemplary techniques for manufacturing chitosan-lecithin composite particles.

For the present disclosure, a particle size distribution by number or a particle size distribution size by mass refers to a 'macrosample' containing at least 0.1 gram of sample or at least 0.5 grams or at least 1 gram of sample An First Exemplary Method of Manufacturing the Composite Particles Reference is now made to FIG. 1 which is a flow chart of an exemplary technique for manufacturing chitosan-lecithin composite particles. In step S201, a first solution is formed by dissolving chitosan about 1.5% w/w in 0.75% HCL and mixing for one or more hours to form a first solution.

In some embodiments, there may be a minimum mixing time required in order for the latter-formed composite particles to be soluble in the stomach. In one example, for "low molecular weight" chitosan, a minimum mixing time of one hour is required, while for "medium molecular weight" chitosan, a minimum mixing time of two hours is required, while for "high molecular weight" chitosan, a minimum mixing time of three hours is required In some embodiments, the amount of mixing time is a function of the "strength" of the mixing—for example, under vigorous mixing less time may be required, while if only gently mixed, more time may be required.

In one example, the mixing of step S201 is carried out for at least 20 hours.

In step S203, lecithin at about 7.5% w/w is dissolved in an water to form a second solution.

In step S205 the solutions are mixed together at a given ratio. The ratio of chitosan to lecithin in the composite particles eventually formed may be controlled by controlling the ratio of the first and second solutions. It is during step S205 that the composite particles are formed in solution.

In step S207, the mixed solutions including the composite particles are spray dried to a powder form. It is noted that the size of the composite particles may be controlled, for example, by controlling the temperature of the solution in step S205, and the amount of time the particles are allowed to remain in the solution before spray drying 207.

The present inventor has found that mixing the first and second solutions for 15 minutes at 25 degrees Celsius gets good results, with a significant fraction of particles in the desired 0.3-1.5 micron, or the desired 0.3-2 micron range.

Not wishing to be bound by theory, it is noted that that the size of particles produced by mixing of chitosan and lecithin may increase with mixing time and with reaction temperature. Particles which are too large may be not stable enough at pH 7, and may precipitate at intestinal pH before binding of bile salts can occur. Mixing for too long or at too high of temperature may yield compound particles that are too large.

Thus, in some embodiments, mixing time of step S205 is limited to no greater than 5 minutes, at a temperature of 50° C., or to 10 minutes at 40° C.

A Second Exemplary Method of Manufacturing the Composite Particles

Figure 2:
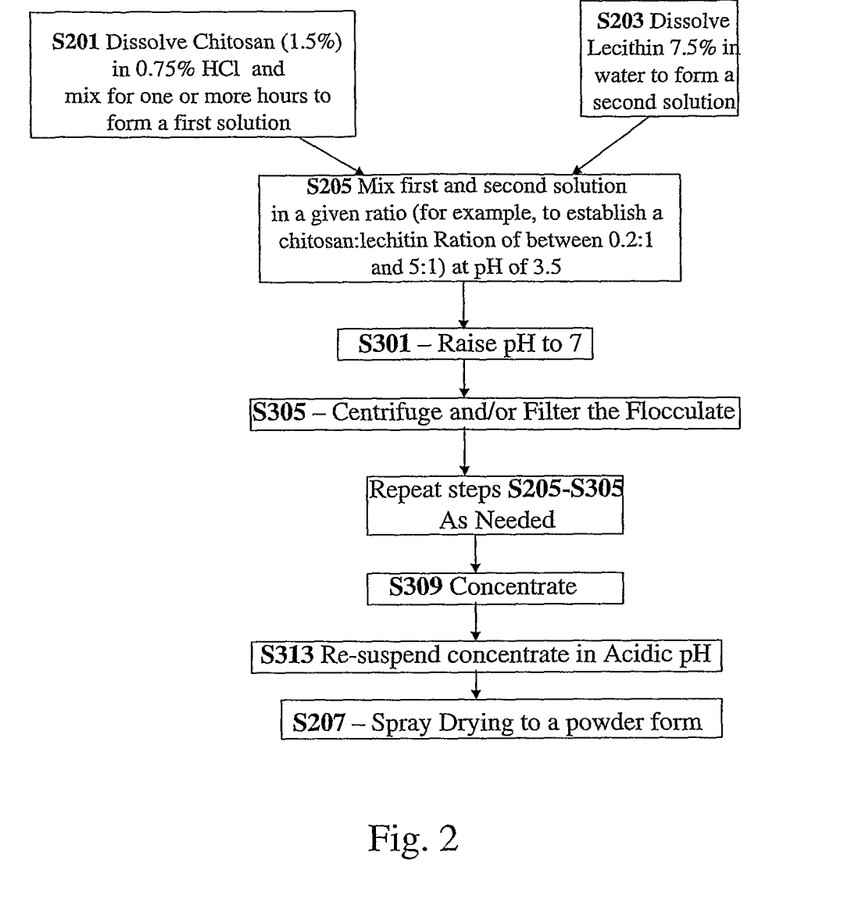

In the technique of FIG. 2, steps S201 and S203 are as in the technique of FIG. 1. In step S205, the solutions are mixed at a given ration, for example, a ratio wherein the mass ratio between lecithin and chitosan is between 3:1 and 4:1. At this point, chitosan and lecithin may bound ionically.

In step S301, the pH is raised to 7, which facilitates formation of a second bond (i.e. a hydrophobic bound) between the chitosan and the lecithin, and wich may faciliate precipation. This may be allowed to occur, for example, for about 30 minutes.

In step S305, the flocullate is centrifuged and filtered to obtain a pellet. Steps 205-S305 may be repeated in order to concentrate S309 the particles. In steps S313, the pellet is then re-supsended in acidic pH, and in step S207 the particles are spray dried to a powder form.

A Method of Mixing the Composite Particles With Animal Feed

The composite particles are mixed with a nutritionally dense animal feed (i.e. nutritionally dense in protein-derived calories and/or carobohydrate-derived calories). In one example, the animal feed is chicken feed. The feed contains between 0.1% and 1% (w/w) composite particle.

In different examples, the nutritionally dense feed can be any common chicken or animal feed or the combination thereof, for example: Broiler, Crumbles, Grower, Layer, Mash, Pellets, Scratch, or Starter. The feed ingredients generally containing one or more of: Amino acid, Bran, Calcium, Concentrate, Corn, Element, Germ, Grain, Grit, Kelp, Middlings, Minerals, Protein, Trace elements, Vitamins, and specifically, having at least 100 kilocalories per 100 gram.

It is recognized that the feed used will vary according to the target animal to be feed enriched animal feed enriched with composite particles.

Alternative Surfactants

According to any of the embodiments of the present invention, any anionic or non-ionic surfactant may be used. Examples of suitable anionic surfactants include phospholipids; bile salts; sodium lauryl ether sulfate; citric acid esters of monoglycerides; sodium, calcium or acid stearoyl lactylate; stearyl citrate; fatty acids or salts thereof; diacetyl tartaric acid esters of monoglycerides; or combinations thereof. Examples of non-ionic surfactants include cetyl alcohol or oleyl alcohol.

In some embodiments, the anionic surfactant comprises the phospholipids, lecithin (phosphatidylcholine), also known as 1,2-diacyl-sn-glycero-3-phosphocholine, or Ptd-Cho, which is represented by the following chemical structure:

R and $R^1$ = fatty acids residues

The term lecithin itself has different meanings when used in chemistry and biochemistry than when used commercially. Chemically, lecithin is phosphatidylcholine. Commercially, it refers to a natural mixture of neutral and polar lipids. Phosphatidylcholine, which is a polar lipid, is present in commercial lecithin in concentrations of 20 to 90%. Most of the commercial lecithin products contin about 20% phosphatidylcholine.

Lecithins containing phosphatidylcholine are produced from vegetable, animal and microbial sources, but mainly from vegetable sources. Soybean, sunflower and rapeseed are the major plant sources of commercial lecithin. Soybean is the most common source. Plant lecithins are considered to be GRAS (generally regarded as safe). Egg yolk lecithin is not a major source of lecithin in nutritional supplements. Eggs themselves naturally contain from 68 to 72% phosphatidylcholine, while soya contains from 20 to 22% phosphatidylcholine.

The fatty acid makeups of phosphatidylcholine from plant and animal sources differ. Saturated fatty acids, such as palmitic and stearic, make up 19 to 24% of soya lecithin; the monounsaturated oleic acid contributes 9 to 11%; linoleic acid provides 56 to 60%; and alpha-linolenic acid makes up 6 to 9%. In egg yolk lecithin, the saturated fatty acids, palmitic and stearic, make up 41 to 46% of egg lecithin, oleic acid 35 to 38%, linoleic acid 15 to 18% and alpha-linolenic 0 to 1%. Soya lecithin is clearly richer in polyunsaturated fatty acids than egg lecithin. Unsaturated fatty acids are mainly bound to the second or middle carbon of glycerol.

Lecithin may have a number of advantages over other surfactants. For example, lecithin is an intrinsic part of the bile salt complex, it is cheap, and it is well recognized by bile acids.

Preferably, the anionic surfactant comprises lecithin (phosphatidylcholine), a phospholipids which is the major component of a phosphatide fraction which may be isolated from egg yolk or soy beans. Lecithin has a number of advantages over other surfactants. For example, lecithin is an intrinsic part of the bile salt complex, it is cheap, and it is well recognized by bile acids.

Alternatives for Chitosan

As an alternative to chitosan in any of the embodiments of the present invention, any suitable positively charged polymer may be used. Examples of suitable positively charged polymers include polyamines such as polylysine and polyamidoanine. According to any of the embodiments of the present invention, high molecular weight chitosan is preferably used, since low molecular weight chitosan has low hydrophobicity, and is therefore less effective in the mixture of the present invention. The preferred range for high molecular weight chitosan is about $5\times10^5$-$3\times10^6$ daltons.

The ratio of lecithin to chitosan in the composite particles may vary based on one or more factors, such as the molecular weight of the chitosan and/or the type of lecithin used. In some embodiments, the ratio is optionally in the range from about 1:0.2 to about 5:1, when using phospholipid rich lecithin. Hence, the range may comprise, for example, 0.2:1, 0.25:1, 0.4:1, 0.6:1, 1:1, 1.2:1, 2:1, 2.8:1, 3:1, 4:1 or 5:1. More preferably, the range is from about 3:1 to about 4:1, such as, for example, 3:1, 3.3:1, 3.5:1, 3.7:1 or 4:1.

The concentration of chitosan in the mixture is optionally no greater than about 1% (w/w), such as, for example, about 0.1%, about 0.2%, about 0.25%, about 0.3%, about 0.4%, about 0.5%, about 0.6%, about 0.7%, about 0.8%, about 0.9%, or about 1% or about 1.3% or about 1.5% or about 1.7% or about 2% about 2.5%. (w/w).

The concentration of lecithin in the mixture is optionally in the range of from about 0.1% to about 7.5% (w/w) or in any subrange thereof.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in tie art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

EXAMPLES

Materials and Methods

Materials

Low molecular weight chitosan 100,000 g/mol (SK-10), having a degree of acetylation of 20% and high molecular weight chitosan, $2.8 \times 10^6$ g/mol (SK-100), having a degree of acetylation of 9% were obtained from Koyo, Japan.

Partially hydrolyzed lecithin, resulting in a rich phospholipid (HL 50 IP) was obtained from Cargill, Germany.

Method of Preparation a. SK-10 Chitosan

Solutions of low molecular weight SK-10 chitosan (1%) in 0.5% HCl and lecithin (10%) in water were prepared by stirring for 24 hours at 25° C. The pH of each solution was adjusted to 3.2.

The two solutions were mixed for 15 minutes at 25° C. at the following lecithin: chitosan ratios: 1:1, 2:1; 3:1; 4:1; and 5:1 to form a suspension.

Samples were withdrawn in order to study the size distribution and zeta potential of the particles thus formed. Results are shown in Table 1.

The suspension was stirred for one hour and than transferred to a spray dryer (BUCHI mini spray dryer B-290). The temperature at the entrance of the spray dryer was 120° C., the degree of the aspirator was 70% and the pumping degree was 25%.

The powder that formed was first resuspended in hydrochloric acid (pH 3.0) to form a suspension of particles comprising chitosan at a concentration of 0.25% w/w, with varying concentrations of lecithin, to provide different ratios of lecithin:chitosan, as follows:

| Ratio of lecithin/SK-10 chitosan in the powder | Concentration of the lecithin in the dispersion (% weight) |
| --- | --- |
| 0.6 | 0.15 |
| 1.2 | 0.3 |
| 2.8 | 0.7 |
| 4 | 1 |
| 5 | 1.25 |

0.25 g was removed from each of the powders obtained and resuspended in 20 ml HCl (pH 3.0) for 30 mins, to simulate conditions in the human stomach. The solutions were then neutralized with NaOH and 30 ml phosphate buffer containing (in mM): 108 NaCl, 4.7 KCl, 1.8 $NaH_2PO_4$, 15 $NaHCO_3$, 12$MgSO_4$, 1.25 $CaCl_2$, to bring the pH of the solution to 6.8, which simulates human intestinal conditions.

Figure 3:
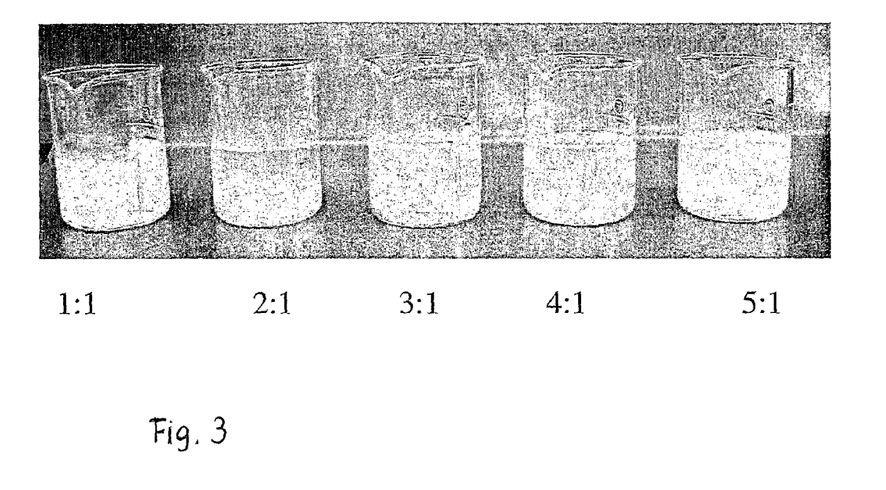
FIGS. 3-4 provides digital images illustrating the dispersion and the stability of the composite particles in phosphate buffer.

The dispersion and the stability of the particles were recorded by digital photography after 3 hours in phosphate buffer. The results are shown in FIG. 3.

b. SK-100 Chitosan

Solutions of high molecular weight SK-100 chitosan (1%) in 0.5% HCl and lecithin (10%) in water were prepared as described above for SK-10.

The powder that formed was first resuspended in hydrochloric acid (pH 3.0) to form a suspension of particles comprising chitosan at a concentration of 0.25% w/w, with varying concentrations of lecithin, to provide different ratios of lecithin:chitosan, as follows:

| Ratio of lecithin/SK-100 chitosan in the powder | Concentration of the lecithin in the dispersion (% weight) |
| --- | --- |
| 1.25 | 0.3 |
| 2 | 0.5 |
| 2.8 | 0.7 |
| 4 | 1 |
| 5 | 1.25 |

Samples were withdrawn in order to study the size distribution of the particles thus formed. Results are shown in Table 2.

0.25 g was removed from each of the powders obtained and resuspended in HCl, then in phosphate buffer at 6.8, as described above with regard to SK-10 chitosan.

Figure 4A:
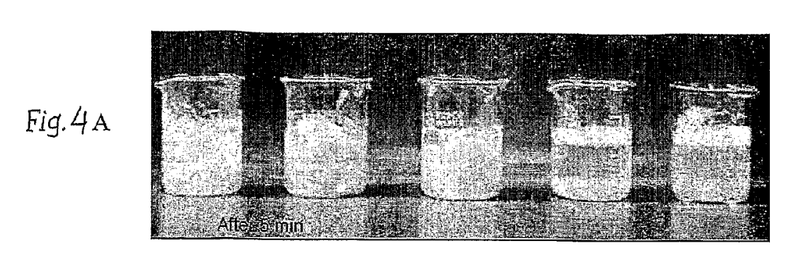
Figure 4B:
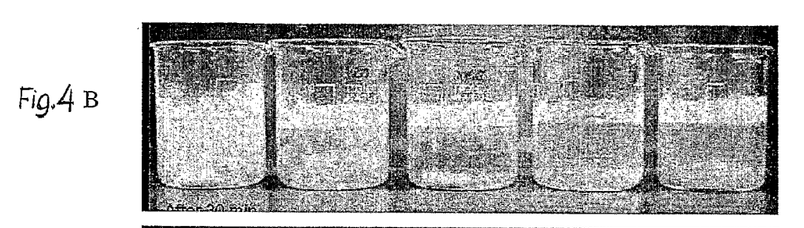
Figure 4C:
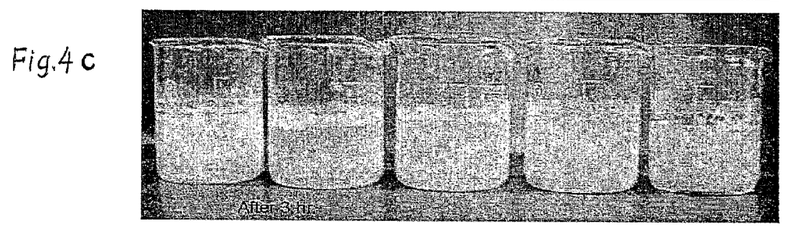

The dispersion and the stability of the particles were recorded by digital photography after 5 minutes (FIG. 4 A) 30 minutes (FIG. 4 B) and 3 hours (FIG. 4 C in phosphate buffer.

In Vitro Model of Interaction Between Chitosan-Lecithin Particles and Bile Acids In order to study the possible interaction between bile acids and the chitosan-lecithin particles of the present invention, an in vitro model was used, based on the assumption that the soluble free bile acid derivative, sodium cholate, will be bound by the particles, such that the amount of sodium cholate in the supernate would be reduced. The method measures the free bile acids that remain in the supernatant after mixing particles of lecithin and chitosan in different ratios with sodium cholate, after centrifugation and filtration to remove bound cholate from soluble, unbound cholate remaining in solution.

Colorimetric analysis of cholate in phosphate buffer was performed as described by Paul et al. (*Journal of Biological Chemistry*, pp. 73-82, 1948) Briefly, the method is based on the color produced when acetic acid solutions comprising cholate are treated with furfural and sulfuric acid. The relationship between absorbance and sodium cholate concentration was first studied in order to establish that colorimetric analysis is a suitable method for measuring cholate concentration. The results are presented in FIG. 5.

High molecular weight (SK-100) chitosan at 0.25% w/w, and pure sodium cholate at 0.5% w/w were used, with different amounts of lecithin, to give the following lecithin:chitosan ratios:

| Ratio of lecithin/chitosan in the powder | Concentration of the lecithin in the dispersion (% weight) |
|---|---|
| 1.25 | 0.3 |
| 2 | 0.5 |
| 2.8 | 0.7 |
| 4 | 1 |
| 5 | 1.25 |

The particles were prepared as described above, and suspended in HCl for 30 minutes. The particles were then transferred to phosphate buffer at pH 6.8 and test solutions prepared by mixing with sodium cholate for 30 minutes. Particles were then centrifuged and filtered in order to separate between the particles and the free cholate in the supernatant, before being subjected to colorimetric analysis. Controls consisted of chitosan-lecithin particles in phosphate buffer, without sodium cholate, which have some absorbance in intestinal media. Colorimetric results are presented in Table 2 below.

Preparation of Lecithin-Chitosan Particles for Animal Feeding

In order to produce sufficient quantities of particles for use in the animal study, a spray drier of capacity 16 liters per hour is used. By using such a spray drier, from about 0.5 to about 1 kg can be produced per day. A solution of chitosan (1%) is dissolved in 1% lactic acid for 24 hours with stirring at 25° C. Lecithin (10%) in water is prepared by stirring for 24 hours at 25° C. The pH of each solution is adjusted to 3.3.

The two solutions are mixed for 5 minutes at 45° C. at lecithin: chitosan ratios of from about 1:1 to about 4:1 and then transferred to a spray drier. Samples of lecithin:chitosan ratios 1:1, 2:1 and 3:1 are dried with 50% maltodextrin in order to obtain dry samples. Samples of ratio 3.5:1 and 4:1 are dried with 80% maltodextrin.

Base Chicken Feed

TABLE 1

| Chicken Feed composition: | |
|---|---|
| Calculated Analysis | Layer Diet |
| Protein %: | 17.0 |
| Ca % | 3.80 |
| Phosphorus % | 0.53 |
| Salt % | 0.30 |
| Energy (kcal/100 g) | 275 |

Feed Mixtures
Feed Mixture 1: Base chicken feed only
Feed Mixture 2: Base chicken feed mixed with chitosan powder mixed at a dosage of 0.25%
Feed Mixture 3: Base chicken feed mixed with chitosan powder mixed at a dosage of 0.4%
Feed Mixture 4: Base chicken feed mixed with (i) chitosan powder mixed at a dosage of 0.1% and (ii) lecithin powder mixed at a dosage of 0.1%
Feed Mixture 5: Base chicken feed mixed with (i) chitosan powder mixed at a dosage of 0.125% and (ii) lecithin powder mixed at a dosage of 0.2%
Feed Mixture 6: Base chicken feed mixed with (i) chitosan powder mixed at a dosage of 0.125% and (ii) lecithin powder mixed at a dosage of 0.3%
Feed Mixture 7: Base chicken feed mixed with chitosan-lecithin powder having a lecithin:chitosan ratio of 2:1 at a dosage of 0.25%
Feed Mixture 8: Base chicken feed mixed with chitosan-lecithin powder having a lecithin:chitosan ratio of 3:1 at a dosage of 0.25%
Feed Mixture 9: Base chicken feed mixed with chitosan-lecithin powder having a lecithin:chitosan ratio of 3.5:1 at a dosage of 0.25%
Feed Mixture 10: Base chicken feed mixed with chitosan-lecithin powder having a lecithin:chitosan ratio of 4:1 at a dosage of 0.25%
Feed Mixture 11: Base chicken feed mixed with chitosan-lecithin powder having a lecithin:chitosan ratio of 4:1 at a dosage of 0.4% The base feed is coarse ground feed, and is identical for all mixtures and meets NRC-94 requirements. Feed mixtures 7, 8, 9 are diluted with 50% malto-dextrins. Feed mixtures 10, 11 are diluted with 80% malto-detrins.

Animal Study Methods: 110 chickens are divided into eleven groups of 10 chickens. The age of all chickens is 74 weeks. The first six groups are control groups that are not fed chitosan-lecithin powder of chitosan-lecithin compsoite particles (i.e. with chitosan chemically bonded to lecithin). The last five groups are fed chitosan-lecithin powder of chitosan-lecithin composite particles.

Study group 1 is fed feed mixture 1; study group 2 is fed feed mixture 2, etc.—the Nth study group is fed the Nth feed mixture where N is an integer between 1 and 11. Chicks are fed approximately 125 grams per day for 45 days. During the course of the experiment, chicken physiology and egg qualities are monitored.

Bird Measurements

The performance of the birds will be evaluated by measuring the following: Lives weight: Birds are individually weighed at start of trial and at the end of the experiment. Feed consumption is calculated per battery cage. Daily Mortality is recorded. Egg production (hen-day production) is recorded daily. Feed efficiency and egg weight are measured weekly (after all eggs were collected for that day)

Egg Quality Measurement

Eggshell quality-% ash is determined—this indicates the thickness of the egg shell. Egg shell quality is tested using following method: After individually weighing the eggs, they are broken, the shells washed and dried at room temperature for the determination of shell weight and shell thickness measured without membranes. All eggs are handled to separate the cracked and checked eggs.

The following criteria are used determine eggshell quality. Chemical Analysis: (according to approved AOAC methods) Moisture (%), Total cholesterol, Yolk Cholesterol, Fatty Acid Profile, MUFA, PUFA SAT, LDL, HDL Results
Particle Size and Zeta Potential at Different Lecithin:chitosan Ratios (SK-10 Chitosan)

The size of the particles formed and their zeta potential at different ratios of lecithin to chitosan is shown in Table 1.

TABLE 1

| Sample no. | lecithin concentration (%) | Ratio (w/w) lecithin/chitosan | Size (microns) | Zeta potential (mV) |
|---|---|---|---|---|
| 1 | 0.05 | 0.2 | 1.2 | +43 |
| 2 | 0.07 | 0.25 | 1.8 | +42 |
| 3 | 0.1 | 0.4 | 1.95 | +42 |
| 4 | 0.3 | 1.2 | 1.25 | +39 |
| 5 | 0.7 | 2.8 | 0.95 | +33 |

The zeta potential represents the charge of the particle. As shown in the Table, zeta potential decreases with increased lecithin:chitosan ratio.
Particle Size at Different Lecithin:chitosan Ratios (SK-100 Chitosan)

Table 2 shows particle size for different concentrations of lecithin. The concentration of chitosan in the experiment is 0.25%. The lecithin:chitosan ratios are therefore 1.2:1; 2:1; 2.8:1; and 4:1.

As shown in the Table, particlesizes generally increase with time and with increased lecithin:chitosan ratio.

| Lecithin concentration (%) | Particle size (nm) after 15 minutes | Particle size (nm) after 1 hour |
| --- | --- | --- |
| 0.3 | 518 | 381 |
| 0.3 | 27 | 379 |
| 0.5 | 526 | 1030 |
| 0.5 | 771 | 1010 |
| 0.7 | 574 | 861 |
| 0.7 | 25.2 | 773 |
| 1 | 938 | 1270 |
| 1 | 905 | 1460 |
| 1.25 | 1170 | 1180 |
| 1.25 | 1240 | 785 |

Dispersion and Stability of Particles at Different Lecithin:chitosan Ratios

FIG. 3 shows dispersion of the SK-10 particles after 3 hours in phosphate buffer at lecithin:chitosan ratios of 1:1, 2:1, 3:1, 4:1 and 5:1.

FIGS. 4A-4C show dispersion of SK-100 particles, after 5 minutes, 30 minutes and 3 hours in phosphate buffer. As shown in FIG. 4A-4C, articles were stable at a ratio of 1:1 lecithin:chitosan, and did not precipitate with time over at least 3 hours. The average size of these particles was found to be around 300-400 nano microns. As the lecithin:chitosan ratio was increased, it was found that particle size ranging from several hundred nanometers to one or two microns were obtained, and the particles lost their stability in the solution and begin to precipitate.

Precipitation of particles increased in proportion to the increase in the lecithin:chitosan ratio, as the result of increasing the hydrophobic portion of the particles. However, it is considered that too rapid precipitation of particles would not enable sufficient time for the particles to interact with bile acids, hence it is concluded that a ratio of from about 3:1 to about 4:1 is preferable.

In Vitro Model of Interaction between Chitosan-lecithzin Particles and Bile Acids.

In order to study the possible interaction between bile acids and the chitosan-lecithin particles of the present invention, an in vitro model was used, based on the assumption that the soluble free bile acid derivative, sodium cholate, will be bound by the particles, such that the amount of sodium cholate in the supernate would be reduced. The method measures the free bile acids that remain in the supernatant after mixing particles of lecithin and chitosan in different ratios with sodium cholate, after centrifugation and filtration to remove bound cholate from soluble, unbound cholate remaining in solution.

Colorimetric analysis of cholate in phosphate buffer was performed as described by Paul et al. (*Journal of Biological Chemistry*, pp. 73-82, 1948) Briefly, the method is based on the color produced when acetic acid solutions comprising cholate are treated with furfural and sulfric acid. The relationship between absorbance and sodium cholate concentration was first studied in order to establish that colorimetric analysis is a suitable method for measuring cholate concentration. The results are presented in FIG. 5.

Figure 5:
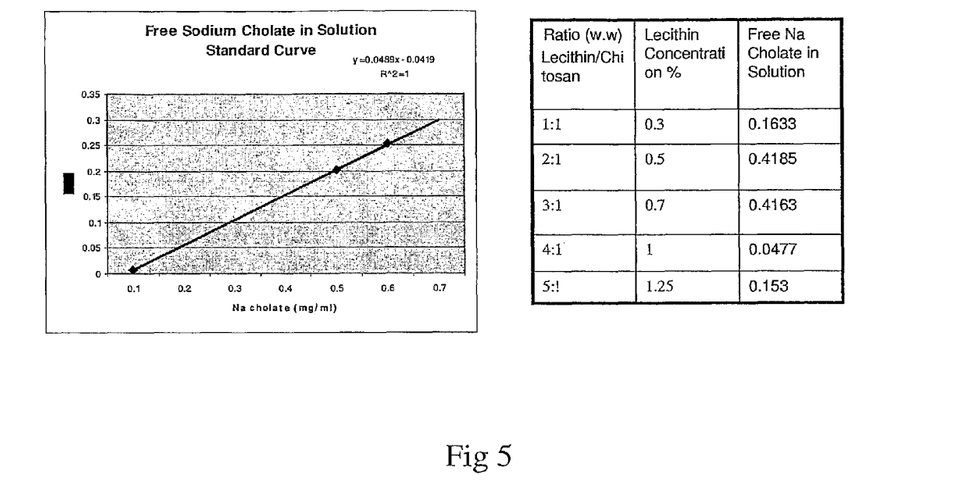
FIG. 5 presents data describing removal of free sodium cholate, by chitosan-lecithin composite particles, from sodium cholate solution.

As shown in FIG. 5, a linear relationship was established between sodium cholate concentration in solution (mg/ml) and absorbance by colorimetric analysis, showing that this method is suitable for measurement of cholate concentration.

The results of calorimetric analysis of test solutions are shown in Table 3 below.

TABLE 3

| Lecithin (%) | control | treatment | Treat – Con |
| --- | --- | --- | --- |
| 0.3 | 0.1549 | 0.3182 | 0.1633 |
| 0.5 | 0.1956 | 0.6141 | 0.4185 |
| 0.7 | 0.2235 | 0.6398 | 0.4163 |
| 1 | 0.3547 | 0.4024 | 0.0477 |
| 1.25 | 0.2786 | 0.4316 | 0.153 |

As shown in the Table, increased lecithin content led to increased binding of cholate by the chitosan-lecithin particles, such that less cholate remained in the supernatant. Increasing the lecithin content in the particles increased the hydrophobic character of the particles, thereby improving the affinity of the particles for the hydrophobic site of the sodium cholate.

From the results of Table 3, the amount of cholate in mg remaining in solution at lecithin:chitosan ratios of 2:1 and 3:1 was calculated, based on an OD of 0.4185 being equal to 0.74 mg sodium cholate. It was found that 40% of this amount remained at a ratio of 1:1, 12% of this amount at 4:1, and 37% at 5:1. Hence, 60%, 88% and 63% of cholate is absorbed at ratios of 1:1 4:1 and 5:1, respectively.

It was further found that for particles having a lecithin:chitosan ratio of about 1:1, the effect of size is more significant than that of hydrophobic degree. Since nanoparticles (of diameter about 0.4 µm) have a high surface area these are more soluble, but less hydrophobic than the particles formed at higher ratios. These particles absorbed about 60% sodium cholate. However, bile salts which are absorbed by these nanoparticles will not be able to pass through the intestine without undergoing further hydrolysis, but will instead quickly separate from the particles and remain in the intestinal tract. Hence, it is desirable to use microparticles for the mixture of the present invention.

It is concluded that the in vitro test for measuring the degree of absorption of bile salts is not sufficient for quantification of the amount of bile salts which is trapped by the particles and subsequently expelled from the body via the feces. In vivo animal studies are required to accurately quantify the amount of bile salts expelled in the feces.

Expected Results for Chicken Experiments

After fine-tuning the optimum feed additive concentration in bird feed, the expected result is a reduction of up to 30% in a chicken egg's LDL content.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

All references cited herein are incorporated by reference in their entirety. Citation of a reference does not constitute an admission that the reference is prior art.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to.

The term "or" is used herein to mean, and is used interchangeably with, the term "and/or," unless context clearly indicates otherwise.

The term "such as" is used herein to mean, and is used interchangeably, with the phrase "such as but not limited to".

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

What is claimed is:

1. A mixture useful for cholesterol treatment, the mixture comprising a plurality of hydrophobic composite particles, each said composite particle consisting of a chitosan and lecithin, said chitosan is non-covalently bound to a lecithin by at least hydrophobic interactions, wherein
    said composite particles having a lecithin-chitosan mass ratio of between 3:1 and 5:1, and wherein
    when the hydrophobic composite particles are introduced into a medium having a pH of about 6.8:
    (i) said hydrophobic composite particles remain as stable particle suspension in the medium;
    (ii) said hydrophobic stable composite particles agglomerate with bile salts in said medium and precipitate together with said bile salts.

2. The mixture of claim 1 wherein said composite particles of said mixture are capable, upon mixing 2.5 grams of said composite particles of said mixture with 1 liter of a sodium cholate solution having a sodium cholate concentration of 0.5% w/w, of removing at least 35% of free sodium cholate from said sodium cholate solution within 30 minutes.

3. The mixture of claim 1 further comprising:
    c) chicken feed, wherein a sum of a protein-derived and a carbohydrate-derived nutritional value of said mixture is at least 2 calories per gram of said mixture.

4. The mixture of claim 1 wherein said chitosan has a molecular weight in the range of from $0.5 \times 10^6$ to $3 \times 10^6$ daltons.

5. A method of obtaining low-cholesterol eggs, the method comprising:
    a) putting chickens on a diet that includes an animal feed product mixed with the mixture of claim 1; and
    b) obtaining the low-cholesterol eggs from the chickens.

6. A method of producing chitosan lechitin composite particles, the method comprising:
    a) providing a plurality of chitosan particles;
    b) mixing said plurality of chitosan particles into an acid to obtain a first solution;
    c) preparing a second solution comprising lecithin;
    d) mixing said first and second solutions under acidic conditions to form chitosan lecithin composite particles consisting of a chitosan and lecithin, wherein said composite particles having a lecithin-chitosan mass ratio of between 3:1 and 5:1; and
    e) forming a powder from said chitosan lecithin composite particles such that said chitosan and lecithin bounded non-covalently by at least hydrophobic interactions.

7. The method of claim 6 wherein:
    said composite particles of said powder are further bound by ionic interactions.

8. The method of claim 6 wherein said powder forming of step (e) includes spray-drying technique.

9. The method of claim 6 wherein said mixing of step (d) is carried out at a temperature and mixing time duration so that at least 10% by mass of said formed composite particles have a size that is between 0.3 and 2 microns.

10. The method of claim 6, wherein a concentration of said chitosan in said mixture of said first solutions is between 0.1% w/w to 2% w/w.

11. The method of claim 6, wherein said mixture of said second solution includes lecithin, and a concentration of said lecithin in said mixture of said second solutions is between 0.1% w/w to 7.5% w/w.

12. A method for increasing cholesterol reduction by chitosan particles, the method comprising increasing the hydrophobicity of said chitosan particles by mixing chitosan particles with lecithin to form chitosan-lecithin composite particles in which the chitosan is non-covalently bound to the lecithin by at least hydrophobic interactions, wherein
    said composite particles having a lecithin-chitosan mass ratio of between 3:1 and 5:1, and wherein
    when said chitosan composite particles are introduced into a medium having a pH of about 6.8:
    (i) said chitosan composite particles remain as stable particle suspension in the medium; and
    (ii) said chitosan stable composite particles agglomerate with said bile salts in said medium and precipitate with said bile salts in said intestinal medium.

13. The method of claim 12, wherein said chitosan composite particles consist of only said chitosan and said lecithin.

* * * * *